(12) United States Patent
Tukuda et al.

(10) Patent No.: US 9,358,160 B2
(45) Date of Patent: Jun. 7, 2016

(54) APPARATUS AND METHOD FOR PRODUCING ABSORBENT

(75) Inventors: Atushi Tukuda, Kanonji (JP); Seiji Murakami, Kanojii (JP)

(73) Assignee: UNICHARM CORPORATION, Shikokuchuo-shi, Ehime (JP)

( * ) Notice: Subject to any disclaimer, the term of this patent is extended or adjusted under 35 U.S.C. 154(b) by 239 days.

(21) Appl. No.: 14/001,351

(22) PCT Filed: Jan. 26, 2012

(86) PCT No.: PCT/JP2012/051696
§ 371 (c)(1),
(2), (4) Date: Aug. 23, 2013

(87) PCT Pub. No.: WO2012/114823
PCT Pub. Date: Aug. 30, 2012

(65) Prior Publication Data
US 2013/0328233 A1 Dec. 12, 2013

(30) Foreign Application Priority Data
Feb. 25, 2011 (JP) ................................ 2011-040330

(51) Int. Cl.
*B29C 43/46* (2006.01)
*A61F 13/15* (2006.01)
*B29C 43/22* (2006.01)

(52) U.S. Cl.
CPC ....... *A61F 13/15674* (2013.01); *A61F 13/1565* (2013.01); *B29C 43/22* (2013.01); *B29C 43/46* (2013.01)

(58) Field of Classification Search
None
See application file for complete search history.

(56) References Cited

U.S. PATENT DOCUMENTS 3,366,115 A * 1/1968 Champaigne, Jr. ..................... A61F 13/15682
156/176
4,216,687 A * 8/1980 Passafiume ....... A61F 13/15723
264/160

(Continued)

FOREIGN PATENT DOCUMENTS

EP 2255765 A1 12/2010
JP 2010136899 A 6/2010

(Continued)

OTHER PUBLICATIONS

Corresponding International Application No. PCT/JP2012/051696 Search Report dated Mar. 19, 2012.

*Primary Examiner* — Edmund Lee
(74) *Attorney, Agent, or Firm* — Hauptman Ham, LLP

(57) ABSTRACT

An apparatus for producing an absorbent is provided with a stacking unit which sequentially forms a plurality of stacks S and discharges these stacks in the machine direction separated by gaps, pattern plates respectively having deep recesses so that thick parts are formed around back ends of the stacks in the machine direction, a wrapping unit which wraps the stacks which are sequentially discharged from the stacking unit by a wrapping web to thereby form continuous wrapped stacks, a conveying unit which conveys the continuous wrapped stacks in the machine direction, a pressing unit which presses the conveyed continuous wrapped stacks to stretch the stacks and thereby form connected parts C at which adjoining stacks are connected, and a cutting unit which cuts the continuous wrapped stacks at the connected parts C to thereby form the absorbents into predetermined shapes.

9 Claims, 7 Drawing Sheets

(56) References Cited

U.S. PATENT DOCUMENTS

| | | | | |
|---|---|---|---|---|
| 4,274,318 A | * | 6/1981 | Passafiume | A61F 13/15723 425/83.1 |
| 2003/0212376 A1 | | 11/2003 | Walter et al. | |
| 2012/0018078 A1 | | 1/2012 | Ishikawa | |

FOREIGN PATENT DOCUMENTS

| | | |
|---|---|---|
| JP | 2010136900 A | 6/2010 |
| JP | 2010178919 A | 8/2010 |
| WO | 2004/028426 A1 | 4/2004 |

* cited by examiner

APPARATUS AND METHOD FOR PRODUCING ABSORBENT

RELATED APPLICATIONS

The present application is a National Phase of International Application Number PCT/JP2012/051696, filed Jan. 26, 2012, and claims priority from Japanese Application Number 2011-040330, filed Feb. 25, 2011.

TECHNICAL FIELD

The present invention relates to an apparatus and method for producing an absorbent.

BACKGROUND ART

In the past, there has been known an apparatus for producing an absorbent which is used for producing an absorbent product, which apparatus for producing an absorbent including a stacking unit which sequentially forms a plurality of stacks and discharges these stacks in a machine direction separated by gaps, a wrapping unit which wraps the stacks which are sequentially discharged from the stacking unit by a wrapping web to thereby form continuous wrapped stacks, a conveying unit which conveys the continuous wrapped stacks in the machine direction, and a cutting unit which cuts the continuous wrapped stacks to form predetermined shapes of absorbents.

Here, the stacking unit for example includes a rotary drum, a plurality of pattern plates which are held at the outer circumferential surface of the rotary drum in a removable state, and a material feeder which feeds the stacking material to the pattern plates (see PTL 1). The shape of pattern plates corresponds to the shape of the stacks which are to be produced. Therefore, by exchanging the pattern plates, it is possible to easily change the shapes of the stacks to be produced.

On the other hand, in the cutting unit, the continuous wrapped stacks are generally cut at the spaces between the adjoining stacks.

CITATIONS LIST

Patent Literature

PTL 1: Japanese Patent Publication No. 2010-178919A

SUMMARY OF INVENTION

Technical Problem

However, gaps are provided between the adjoining stacks. Therefore, the cutting unit cuts the wrapping web without cutting the stacks. In this regard, the wrapping web is comprised of a relatively thin nonwoven fabric or tissue, so it is difficult to reliably cut the wrapping web. Therefore, it is difficult to accurately form the absorbents into predetermined shapes. If raising the cutting pressure to reliably cut the wrapping web, lifetime of the cutting edge of the cutting unit may be shorter.

Solution to Problem

According to a first aspect of the present invention, there is provided an apparatus for producing an absorbent which is used for producing an absorbent product, the apparatus being provided with a stacking unit which sequentially forms a plurality of stacks and discharges these stacks in the machine direction separated by gaps, which stacking unit is provided with a rotary drum, a plurality of pattern plates which are held at the outer circumferential surface of the rotary drum in a removable manner, and a material feeder which feeds stacking materials to the pattern plates, the pattern plates respectively having deep recesses so that thick parts are formed around back ends of the stacks in the machine direction, a wrapping unit which wraps the stacks which are sequentially discharged from the stacking unit by a wrapping web to thereby form continuous wrapped stacks, a conveying unit which conveys the continuous wrapped stacks in the machine direction, a pressing unit which presses the conveyed continuous wrapped stacks to stretch the stacks and thereby form connected parts at which adjoining stacks are connected, and a cutting unit which cuts the continuous wrapped stacks at the connected parts to thereby form the absorbents into predetermined shapes.

According to a second aspect of the present invention, there is provided a method for producing an absorbent which is used for producing an absorbent product, the method comprising a stacking step which uses a stacking unit to sequentially form a plurality of stacks and discharge these stacks in the machine direction separated by gaps, which stacking unit is provided with a rotary drum, a plurality of pattern plates which are held at the outer circumferential surface of the rotary drum in a removable manner, and a material feeder which feeds stacking materials to the pattern plates, the pattern plates respectively having deep recesses so that thick parts are formed around back ends of the stacks in the machine direction, a wrapping step which wraps the stacks which are sequentially discharged from the stacking unit by a wrapping web to thereby form continuous wrapped stacks, a conveying step which conveys the continuous wrapped stacks in the machine direction, a pressing step which presses the conveyed continuous wrapped stacks to stretch the stacks and thereby form connected parts at which adjoining stacks are connected, and a cutting step which cuts the continuous wrapped stacks at the connected parts to thereby form the absorbents into predetermined shapes.

Advantageous Effects of Invention

The continuous wrapped stacks can be reliably cut, so the absorbents can be accurately formed into predetermined shapes.

DESCRIPTION OF EMBODIMENTS

Figure 1:
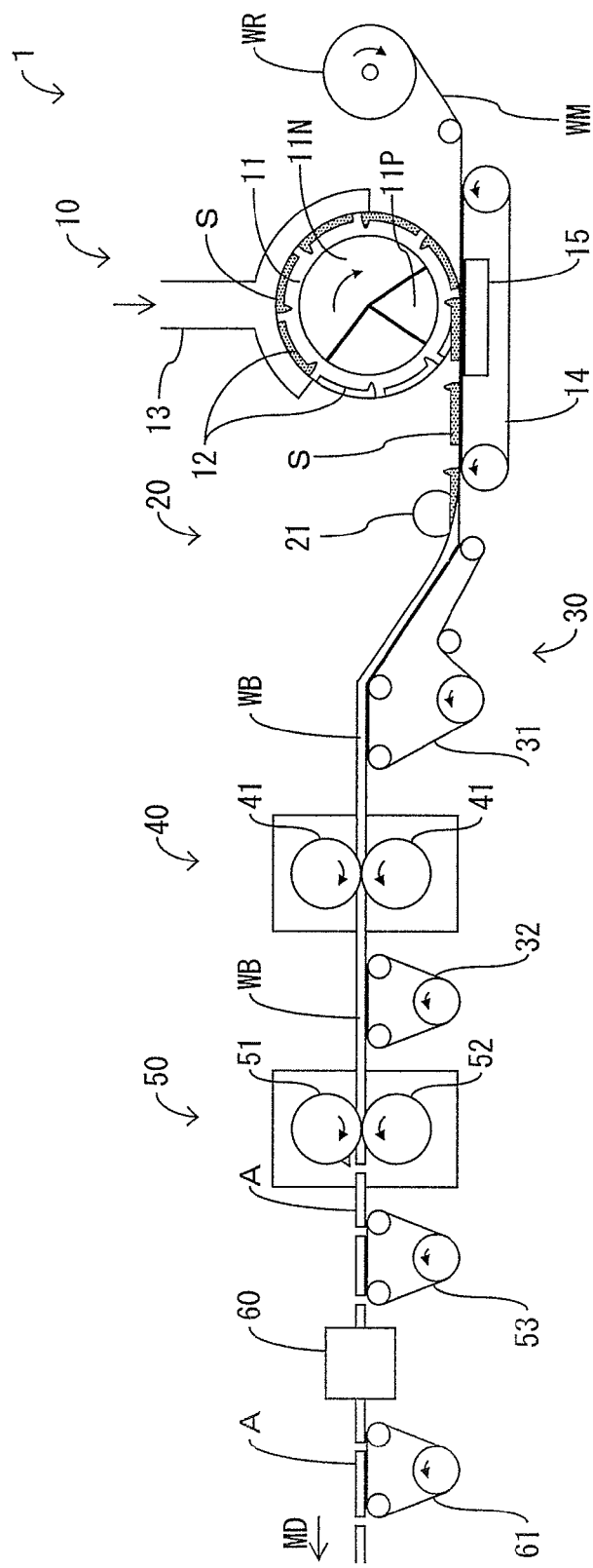
FIG. 1 is a schematic overall view of an absorbent production apparatus.

FIG. 1 shows an apparatus 1 which produces an absorbent which is used for production of an absorbent product. Here, a disposable diaper, sanitary napkin, incontinence pad, etc., are absorbent products.

Referring to FIG. 1, the absorbent production apparatus 1 is provided with a stacking unit 10, wrapping unit 20, conveying unit 30, pressing unit 40, and cutting unit 50.

Figure 2:
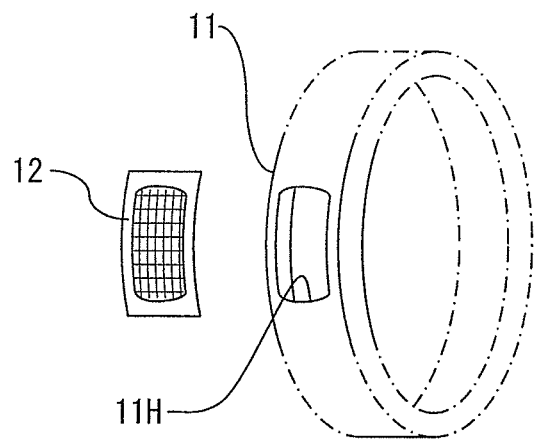
FIG. 2 is a schematic perspective view of a rotary drum and a pattern plate.

Referring to FIG. 1 and FIG. 2, the stacking unit 10 is provided with a rotary drum 11, a plurality of pattern plates 12 which are held at the outer circumferential surface of the rotary drum 11 in a removable manner, and a material feeder 13 which feeds stacking materials to the pattern plates 12.

At the inside space of the rotary drum 11, a negative pressure chamber 11N to which a negative pressure is applied and a positive pressure chamber 11P to which a positive pressure is applied are formed. Further, at the outer circumferential surface of the rotary drum 11, a plurality of through holes 11H which communicate with the negative pressure chamber 11N and the positive pressure chamber 11P are formed.

Figure 3:
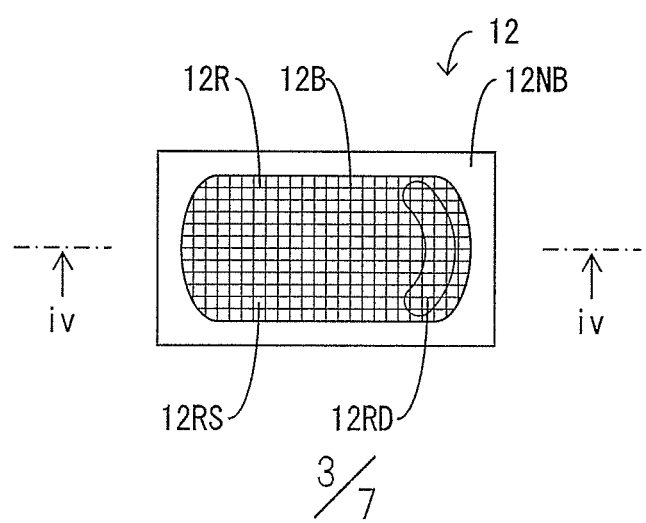
FIG. 3 is a plan view of a pattern plate.
Figure 4:
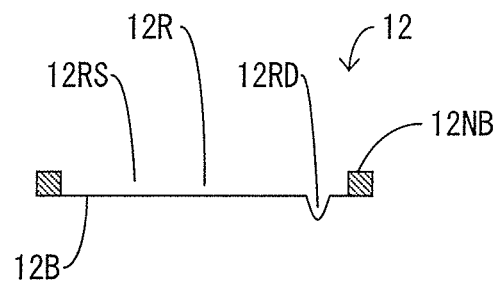
FIG. 4 is a cross-sectional view of a pattern plate seen along the line iv-iv in FIG. 3.

Each pattern plate 12, as shown in FIG. 3 and FIG. 4, includes an air-passing part 12B which receives the stacking material and a non-air-passing part 12NB which surrounds and holds the air-passing part 12B. The air-passing part 12B is for example comprised of a metal mesh, while the non-air-passing part 12NB is for example comprised of a metal plate. The pattern plate 12 is positioned on the rotary drum 11 so that the air-passing part 12B communicates with the through holes 11H of the rotary drum 11, and is for example fastened to the rotary drum 11 by bolts.

The air-passing part 12B and non-air-passing part 12NB define a recess 12R. The recess 12R includes a shallow recess 12RS and a deep recess 12RD. Here, the shape of the recess 12R corresponds to the shape of the stack which is to be produced.

The material feeder 13 feeds stacking material such as pulp fiber, synthetic fiber and an absorbent polymer, in a flying state.

When the rotary drum 11 is made to rotate by a drive mechanism (not shown) in the arrow direction while stacking material is fed from the material feeder 13, the stacking material stacks in the recesses 12R of the pattern plates 12 which are communicated with the negative pressure chamber 11N whereby stacks S are formed in the recesses 12R. Next, when the pattern plates 12 reach the positive pressure chamber 11P together with the stacks S, the stacks S are made to separate from the pattern plates 12.

Again referring to FIG. 1, the wrapping web WM is unrolled from the roll WR. This wrapping web WM is conveyed by the conveyor 14 in the machine direction MD. The stacks S which are separated from the pattern plates 12 are discharged on the wrapping web WM to be conveyed.

Figure 5:
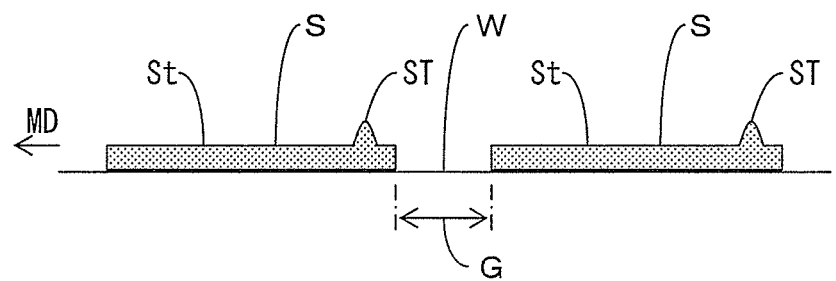
FIG. 5 is a side view of stacks.

In this case, as shown in FIG. 5, the stacks S are conveyed in the machine direction MD separated by gaps G. This is because the non-air-passing parts 12NB of the pattern plates 12 are arranged with the recesses 12R separated by gaps from each other on the rotary drum 11 in the circumferential direction of the rotary drum 11.

In this way, in the stacking unit 10, a plurality of stacks S are sequentially formed and are discharged in the machine direction MD separated by gaps. Note that, in FIG. 1, reference numeral 15 indicates a negative pressure applying apparatus which assists the stacks S in separating from the pattern plates 12.

As shown in FIG. 5, the stacks S include thick parts ST which are formed around the back ends in the machine direction MD and thin parts St other than the thick parts ST. The thick parts ST correspond to the deep recesses 12RD of the pattern plates 12. In other words, the pattern plates 12 have deep recesses 12RD so that thick parts ST are formed around the back ends of the stacks S in the machine direction MD. Note that, it can be seen from the shape of the recess 12R of the pattern plate 12 which is shown in FIG. 3, a thick part ST generally extends in a crossing direction which crosses the machine direction MD.

Figure 6:
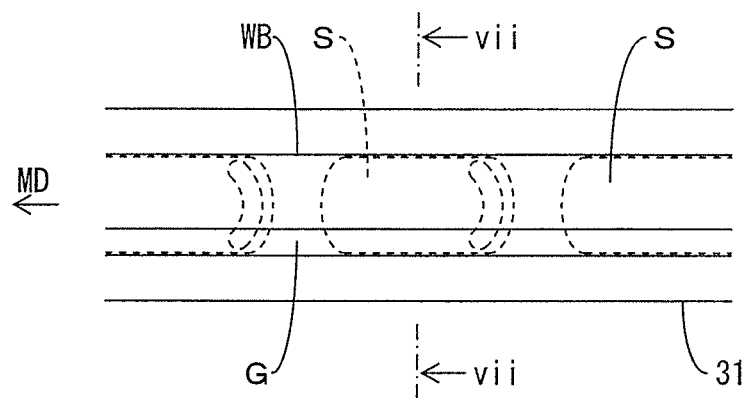
FIG. 6 is a top view of continuous wrapped stacks.
Figure 7:
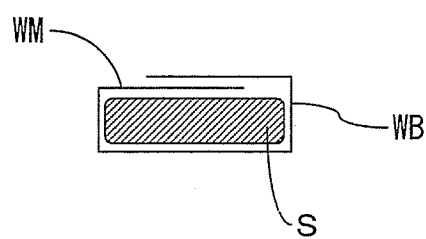
FIG. 7 is a cross-sectional view of continuous wrapped stacks seen along the line vii-vii in FIG. 6.

The stacks S are conveyed to the wrapping unit 20 together with the wrapping web WM. In the wrapping unit 20, the stacks S which are sequentially discharged from the stacking unit 10 are wrapped by the wrapping web WM whereby continuous wrapped stacks WB are formed. That is, the two side edges of the wrapping web WM in the machine direction MD are guided by the guide rolls 21 and superposed with each other. As a result, as shown in FIG. 6 and FIG. 7, the continuous wrapped stacks WB are formed. In this case, as shown in FIG. 6, gaps G remain between the stacks S.

The continuous wrapped stacks WB are next conveyed by the conveyor 31 of the conveying unit 30 in the machine direction MD and conveyed to the pressing unit 40.

Figure 8:
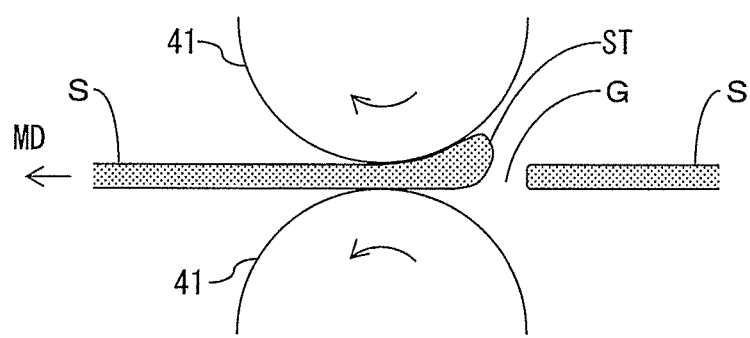
FIG. 8 is a schematic view to explain a pressing action of a pressing unit.
Figure 9:
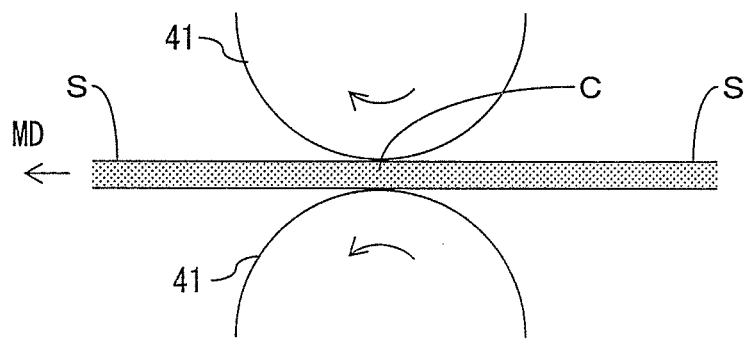
FIG. 9 is a schematic view to explain a pressing action of a pressing unit.

Again referring to FIG. 1, the pressing unit 40 is provided with a pair of pressing rolls 41 which are arranged facing each other. When the continuous wrapped stacks WB are supplied between these pressing rolls 41, the pressing rolls 41 press the continuous wrapped stacks WB and therefore the stacks S. As a result, as shown in FIG. 8, the thick parts ST of the stacks S are stretched in the machine direction MD and are spread in the gaps G between the stacks S. Therefore, as shown in FIG. 9 and FIG. 10, connected parts C which connect the adjoining stacks S with each other are formed.

Figure 10:
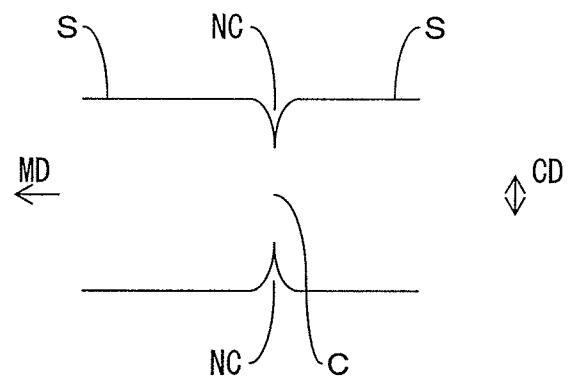
FIG. 10 is a schematic view of a connected part and non-connected parts.

In this embodiment according to the present invention, as shown in FIG. 10, the connected parts C are formed at the centers of the stacks S in the crossing direction, however, are not formed at the two sides in the crossing direction CD. In other words, non-connected parts NC are formed at the two ends of the stacks S in the crossing direction CD. The non-connected parts NC have almost no stacking materials.

The continuous wrapped stacks WB are next conveyed by the conveyor 32 to the cutting unit 50. The cutting unit 50 is provided with a cutter roll 51 and an anvil roll 52 which are arranged facing each other. When the continuous wrapped stacks WB are supplied between the cutter roll 51 and the anvil roll 52, the cutting edge of the cutter roll 51 cuts the continuous wrapped stacks WB whereby predetermined shapes of absorbents A are formed. The absorbents A include single stacks S and wrapping material which wraps the stacks S.

The absorbents A are next conveyed by a conveyor 53 to the sealer 60. At the sealer 60, the two ends of the absorbents A in the machine direction MD are sealed. The sealed absorbents A are next conveyed by the conveyor 61 to the next step. At the next step, the absorbents A are for example assembled with outer packages of the absorbent products.

Note that, the sealer 60 may be used to seal the continuous wrapped stacks WB, then the continuous wrapped stacks WB cut. Therefore, the sealer 60 seals the absorbents A or the continuous wrapped stacks WB so that the two ends of the absorbents A in the machine direction are sealed.

Figure 11:
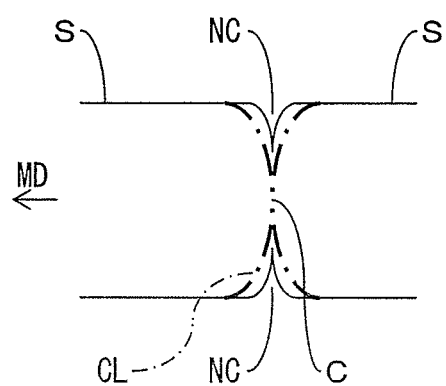
FIG. 11 is a view to explain a cutting action of the cutting unit.

Now, in the cutting unit 50, the continuous wrapped stacks WB are cut at the connected parts C. That is, as shown in FIG. 11, the cutting line CL passes through the connected parts C. As a result, the cutting edge of the cutter roll 51 cuts both the wrapping web WM and the stacks S or stacking material. Therefore, the continuous wrapped stacks WB can be reliably cut and the absorbents A can be accurately formed into predetermined shapes. Further, the cutting pressure does not have to be made excessively high. Therefore, lifetime of the cutting edge can be extended. Note that, in FIG. 8, FIG. 9, FIG. 10, and FIG. 11, illustration of the wrapping web WM is omitted.

Figure 12:
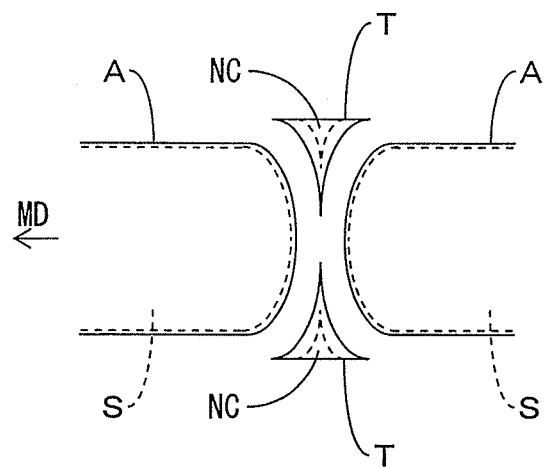
FIG. 12 is a view to explain a cutting action of the cutting unit.

When the continuous wrapped stacks WB are cut, as shown in FIG. 12, for example, two trims T are formed. These trims T are discarded. In the embodiment according to the present invention, the continuous wrapped stacks WB are cut so that the two ends of the absorbents A in the machine direction MD project outward, so the trims become triangular shapes. Here, the trims T include the above-mentioned non-connected parts NC. The non-connected parts NC have almost no stacking materials. As a result, the amount of stacking materials which are discharged can be reduced.

Furthermore, the pattern plates 12 are held at the rotary drum 11 in a removable manner, so the pattern plates 12 can be easily exchanged. Further, the pattern plates 12 respectively have single recesses 12R, so when there is some trouble with the single recesses 12R, the single pattern plates 12 need only be exchanged. Therefore, maintenance of the pattern plates 12 becomes easy.

Figure 13:
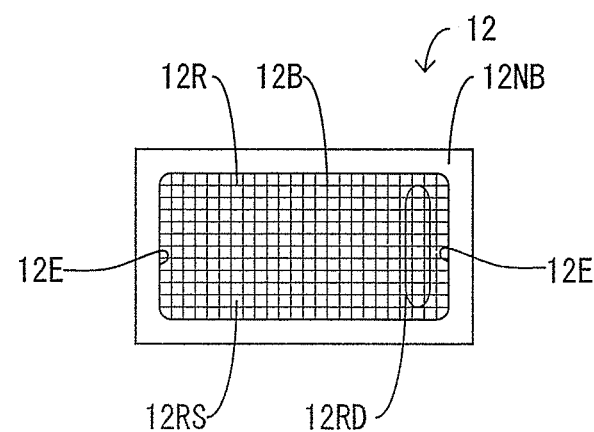
FIG. 13 is a view which shows another embodiment of a pattern plate.

In the embodiment which has been explained up to here, as shown in FIG. 3, the two ends of the recesses 12R of the pattern plates 12 in the machine direction are curved so as to project outward. The deep recesses 12RD are also curved. However, as shown in FIG. 13, the recesses 12R may also be formed so that the two ends 12E of the recesses 12R in the longitudinal directions and the deep recesses 12RD extend on straight lines.

This application claims the benefit of Japanese Patent Application No. 2011-040330, the entire disclosure of which is incorporated here by reference.

REFERENCE SIGNS LIST 1 absorbent production apparatus
10 stacking unit
11 rotary drum
12 pattern plate
12RD deep recess
13 material feeder
20 wrapping unit
30 conveying unit
40 pressing unit
50 cutting unit
A absorbent
C connected part
G gap
S stack
WB continuous wrapped stacks
WM wrapping web

The invention claimed is:

1. An apparatus for producing an absorbent for an absorbent product, the apparatus comprising:
   a stacking unit configured to sequentially form a plurality of stacks separated by gaps and discharge the stacks in a machine direction, said stacking unit including:
      a rotary drum,
      a plurality of pattern plates held at an outer circumferential surface of the rotary drum in a removable manner, and
      a material feeder configured to feed stacking materials to the pattern plates, the pattern plates respectively having deep recesses to form thick parts around back ends of the stacks in the machine direction,
   a wrapping unit configured to wrap the stacks, which are sequentially discharged from the stacking unit, by a wrapping web to form continuous wrapped stacks,
   a conveying unit configured to convey the continuous wrapped stacks in the machine direction,
   a pressing unit configured to press the thick parts of the conveyed continuous wrapped stacks to (i) stretch the stacks in the machine direction, (ii) to spread in the gaps between the stacks among the continuous wrapped stacks, and (iii) to form connected parts at which adjoining stacks are connected, and
   a cutting unit configured to cut the continuous wrapped stacks at the connected parts to form absorbents of a predetermined shape.

2. The apparatus as set forth in claim 1, wherein the pattern plates include
   air-passing parts configured to receive stacking materials, and
   non-air-passing parts surrounding the air-passing parts.

3. The apparatus as set forth in claim 1, wherein the cutting unit is configured to cut the continuous wrapped stacks so that
   two ends of the absorbents opposing in the machine direction project outward in the machine direction, and
   the connected parts do not connect the stacks adjoining each other at two side parts in the crossing direction, but connect the stacks at center parts in the crossing direction.

4. The apparatus as set forth in claim 1, wherein the cutting unit includes a cutter roll and an anvil roll facing each other.

5. The apparatus as set forth in claim 1, wherein the pressing unit includes a pair of pressing rolls facing each other.

6. The apparatus as set forth in claim 1, further comprising a sealer configured to seal the continuous wrapped stacks or the absorbents.

7. The apparatus as set forth in claim 1, wherein the deep recesses of the pattern plates project outward in the machine direction.

8. The apparatus as set forth in claim 1, wherein the absorbent product includes a disposable diaper, sanitary napkin or incontinence pad.

9. A method of producing an absorbent for an absorbent product, the method comprising:
   a stacking step which sequentially forms, by using a stacking unit, a plurality of stacks separated by gaps and discharges the stacks in a machine direction, said stacking unit including:
      a rotary drum,
      a plurality of pattern plates held at an outer circumferential surface of the rotary drum in a removable manner, and a material feeder feeding stacking materials to the pattern plates, the pattern plates respectively having deep recesses to form thick parts around back ends of the stacks in the machine direction, a wrapping step which wraps the stacks sequentially discharged from the stacking unit by a wrapping web to form continuous wrapped stacks, a conveying step which conveys the continuous wrapped stacks in the machine direction, a pressing step which presses the thick part of the conveyed continuous wrapped stacks to (i) stretch the stacks in the machine direction, (ii) to spread in the gaps between the stacks among the continuous wrapped stacks, and (iii) to form connected parts at which adjoining stacks are connected, and a cutting step which cuts the continuous wrapped stacks at the connected parts to form absorbents of a predetermined shape.

* * * * *